`US009733873B2`

(12) United States Patent
Maeda

(10) Patent No.: US 9,733,873 B2
(45) Date of Patent: Aug. 15, 2017

(54) APPARATUS FOR PROCESSING MEDICAL IMAGE WITH TONER SAVE FUNCTION

(71) Applicant: Oki Data Corporation, Tokyo (JP)

(72) Inventor: Masayuki Maeda, Tokyo (JP)

(73) Assignee: Oki Data Corporation, Tokyo (JP)

( * ) Notice: Subject to any disclaimer, the term of this patent is extended or adjusted under 35 U.S.C. 154(b) by 0 days.

(21) Appl. No.: 15/164,286

(22) Filed: May 25, 2016

(65) Prior Publication Data

US 2017/0031637 A1 Feb. 2, 2017

(30) Foreign Application Priority Data

Jul. 30, 2015 (JP) ................................. 2015-150442

(51) Int. Cl.
| | | |
|---|---|---|
| *H04N 1/00* | (2006.01) | |
| *G06F 3/12* | (2006.01) | |
| *H04N 1/38* | (2006.01) | |
| *G06F 19/00* | (2011.01) | |
| *H04N 1/23* | (2006.01) | |
| *H04N 1/387* | (2006.01) | |

(52) U.S. Cl.
CPC .......... *G06F 3/1219* (2013.01); *G06F 3/1208* (2013.01); *G06F 19/321* (2013.01); *H04N 1/38* (2013.01); *H04N 1/2369* (2013.01); *H04N 1/3872* (2013.01); *H04N 2201/0079* (2013.01)

(58) Field of Classification Search
CPC ..................................................... G06F 3/1219
USPC ........................................................ 358/1.6
See application file for complete search history.

(56) References Cited

U.S. PATENT DOCUMENTS

| | | | | |
|---|---|---|---|---|
| 6,999,071 B2* | 2/2006 | Balogh | ............... | G02B 27/2214 |
| | | | | 345/419 |
| 2004/0151358 A1* | 8/2004 | Yanagita | ............... | G06T 7/0012 |
| | | | | 382/132 |
| 2007/0058188 A1 | 3/2007 | Nakahara | | |
| 2007/0115999 A1* | 5/2007 | Qu | ........................ | G06F 19/321 |
| | | | | 370/392 |
| 2010/0128287 A1 | 5/2010 | Harris et al. | | |

(Continued)

FOREIGN PATENT DOCUMENTS

| | | |
|---|---|---|
| JP | 2000289237 A | 10/2000 |
| JP | 2005006885 A | 1/2005 |
| JP | 2007089645 A | 4/2007 |

OTHER PUBLICATIONS

European search report issued on Jan. 3, 2017 in connection with conterpart European Patent Application No. 16171045, 3 pages.

*Primary Examiner* — Jacky X Zheng
(74) *Attorney, Agent, or Firm* — Panitch Schwarze Belisario & Nadel LLP

(57) ABSTRACT

An image processing apparatus includes a setting unit that accepts setting of a first print mode in which printing is performed while saving developer, a data receiver capable of receiving DICOM data in accordance with DICOM standard using a protocol in accordance with the DICOM standard, a determination unit that determines whether received data is DICOM data or not, and an image processing unit that performs processing to print an image. When the received data is DICOM data and when the first print mode is set in the setting unit, the image processing unit performs processing to print a medical image included in the DICOM data in a mode in which developer is saved in a region outside a diagnostic image region necessary for image diagnosis.

15 Claims, 14 Drawing Sheets

(56) References Cited

U.S. PATENT DOCUMENTS

| | | | |
|---|---|---|---|
| 2012/0212758 A1* | 8/2012 | Eom | G06F 3/1204 358/1.13 |
| 2014/0205164 A1 | 7/2014 | Ando et al. | |
| 2015/0261479 A1* | 9/2015 | Park | G06F 3/1219 358/1.9 |

* cited by examiner

APPARATUS FOR PROCESSING MEDICAL IMAGE WITH TONER SAVE FUNCTION

BACKGROUND OF THE INVENTION

The present invention relates to an image processing apparatus such as an image forming apparatus that prints a medical image in accordance with DICOM (Digital Imaging and Communications in Medicine) standard.

A medical image such as an X-ray photograph is taken by a modality (i.e., a medical imaging apparatus). There has been developed technology for printing such a medical image on a medium using an image forming apparatus. A medical image is required to have high quality of black color. For example, a black background of the medical image is required to be deeply printed. Therefore, Japanese Patent Application Publication No. 2000-289237 (see paragraphs 0054-0064) discloses technology for finely controlling depth of black color.

In this regard, an image forming apparatus using electrophotography may have a toner save function, i.e., to print an image with a reduced amount of toner (developer) in order to reduce an operation cost. However, when the medical image is printed using the toner save function, the medical image may entirely become lighter. Particularly, a depth of black color may become lighter. Such a medical image is not suitable for use by a doctor in image diagnosis.

SUMMARY OF THE INVENTION

The present invention is intended to provide an image processing apparatus capable of reducing an amount of developer consumption without lowering a quality of a medical image.

According to an aspect of the present invention, there is provided an image processing apparatus including a setting unit that accepts setting of a first print mode in which printing is performed while saving developer, a data receiver capable of receiving DICOM data in accordance with DICOM standard using a protocol in accordance with the DICOM standard, a determination unit that determines whether received data is DICOM data or not, and an image processing unit that performs processing to print an image. When the received data is DICOM data and when the first print mode is set in the setting unit, the image processing unit performs processing to print a medical image included in the DICOM data in a mode in which developer is saved in a region outside a diagnostic image region necessary for image diagnosis.

With such a configuration, the amount of developer consumption can be reduced, and the quality of the medical image can be maintained.

DETAILED DESCRIPTION OF THE PREFERRED EMBODIMENT

First Embodiment

Hereinafter, the first embodiment of the present invention will be described with reference to the attached drawings.

<Outline>

In a conventional image diagnostic, a doctor diagnoses a medical condition by seeing an analogue image such as a roentgen photograph (i.e., an X-ray photograph) printed on a film. In a recently developed system, DICOM data including digital image data and associated information is created in accordance with DICOM (Digital Imaging and Communications in Medicine) standard, and is transmitted via a network in accordance with the DICOM standard. An image (i.e., image data) included in the DICOM date will be referred to as a DICOM image.

There are cases where a medical image is printed on a medium (for example, a print sheet) by an image forming apparatus such as a printer. In such cases, in order for a doctor to perform image diagnosis as conventionally performed, it is necessary that a depth of a black background (shown by densely distributed dots in FIG. 1A), a gross of a surface and a thickness of the medium are similar to those of the roentgen photograph.

In this regard, the image forming apparatus may have two applications such as a printer for printing a medical image and an OA (Office Automation) printer for printing a general business document. An administrator of the image forming apparatus (i.e., an apparatus administrator) may set a toner save function of the image forming apparatus 100 to ON (enabled) in order to reduce an amount of toner consumption (i.e., developer consumption).

Figure 1:
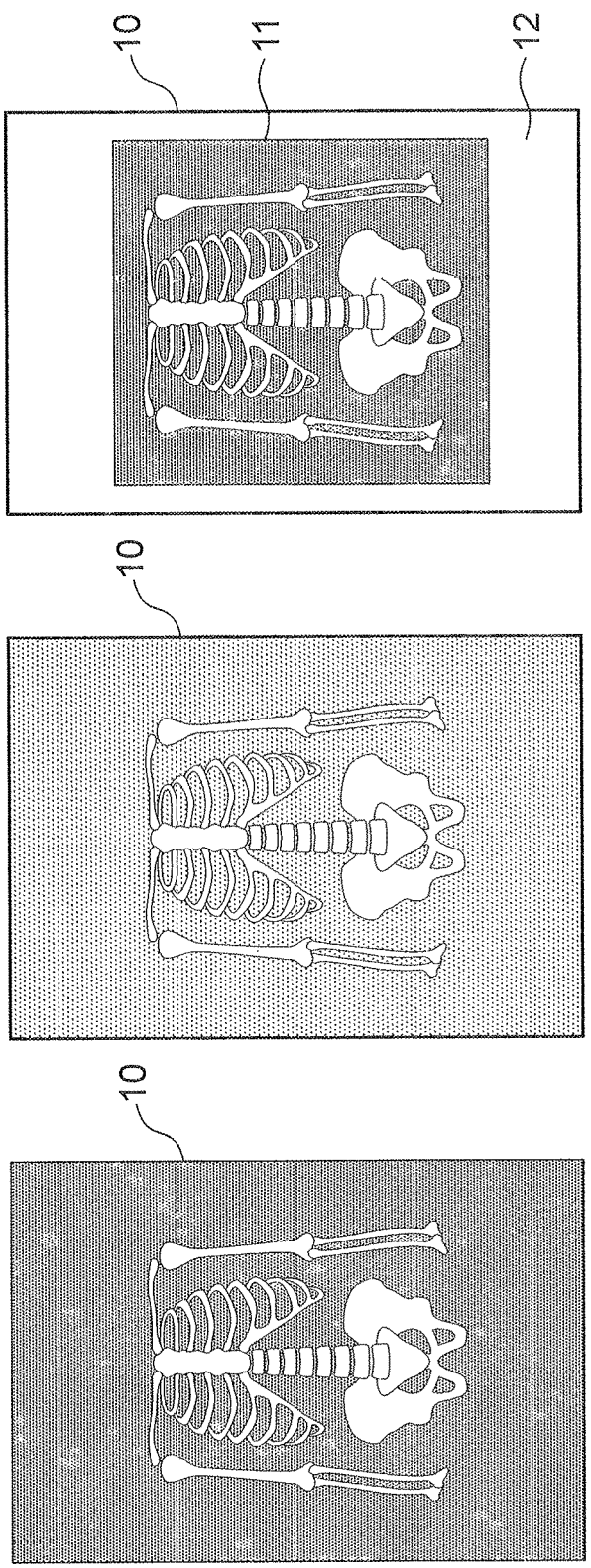
FIGS. 1A, 1B and 1C are schematic views showing an outline of the first embodiment of the present invention.

However, when a medical image is printed in a state where the toner save function is enabled, a printed image entirely becomes lighter as shown in FIG. 1B. To be more specific, the depth of the black background (shown by thinly distributed dots in FIG. 1B) becomes lighter. Such a medical image is not suitable for use by the doctor in image diagnosis.

Figure 10:
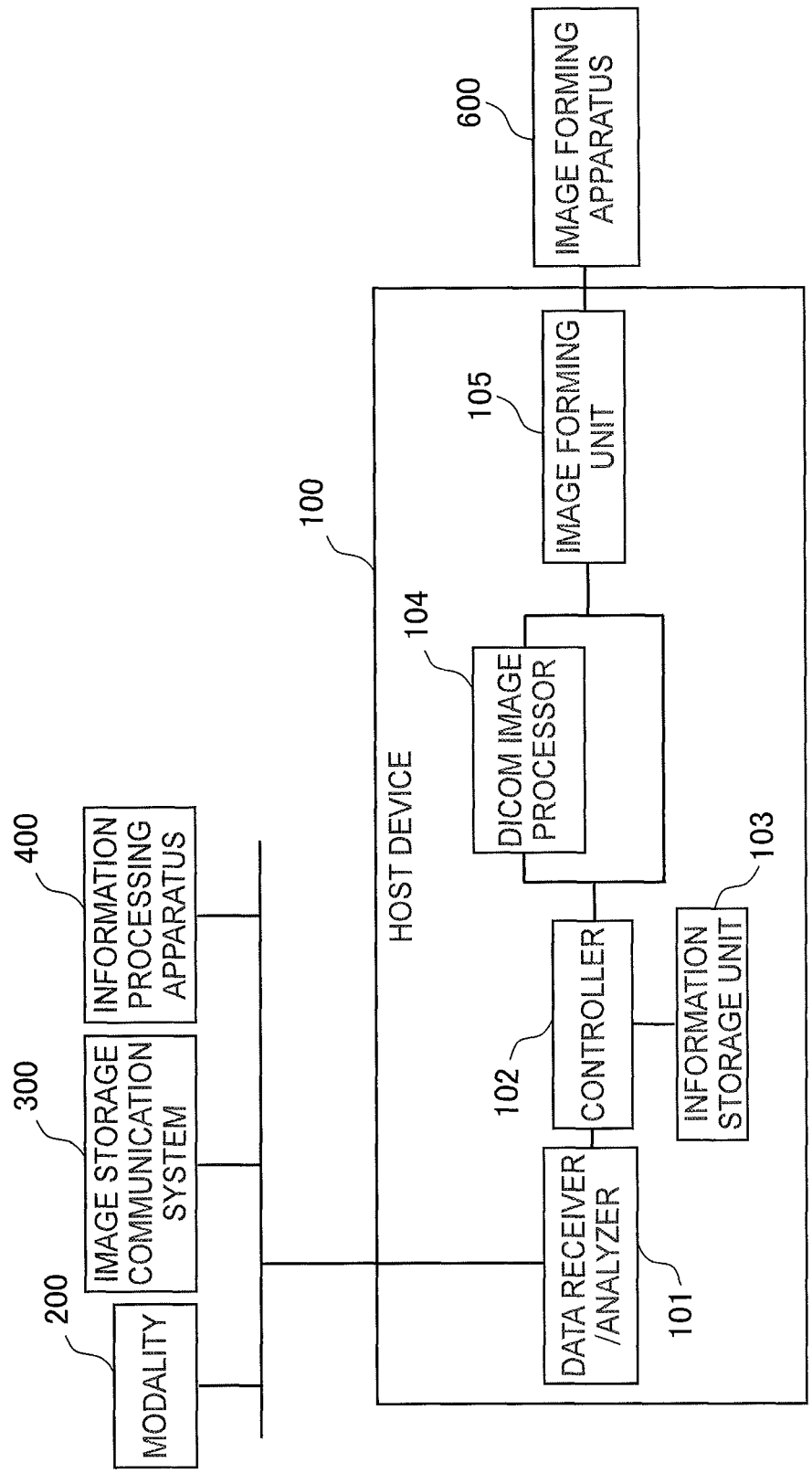
FIG. 10 is a block diagram showing a host device (i.e., an image processing apparatus) and an image forming apparatus of a first modification of the first embodiment.

Therefore, in the first embodiment of the present invention, a region (or a portion) of a medical image 10 to be used by a doctor in image diagnosis (referred to as a diagnostic image region 11) is printed with high quality, i.e., printed without using the toner save function. In contrast, nothing is printed in a region (referred to a margin region 12) outside the diagnostic image region 11 as shown in FIG. 10. The diagnostic image region 11 is printed with high quality, and therefore the black background (shown by densely distributed dots in FIG. 10) of the diagnostic image region 11 is deeply printed. Such an image is suitable for use by the doctor in image diagnosis. Further, since no toner is printed in the margin region 12, an amount of toner consumption can be reduced.

Hereinafter, a configuration of an image forming apparatus 100 as an image processing apparatus of the first embodiment of the present invention will be described.

<Configuration>

Figure 2:
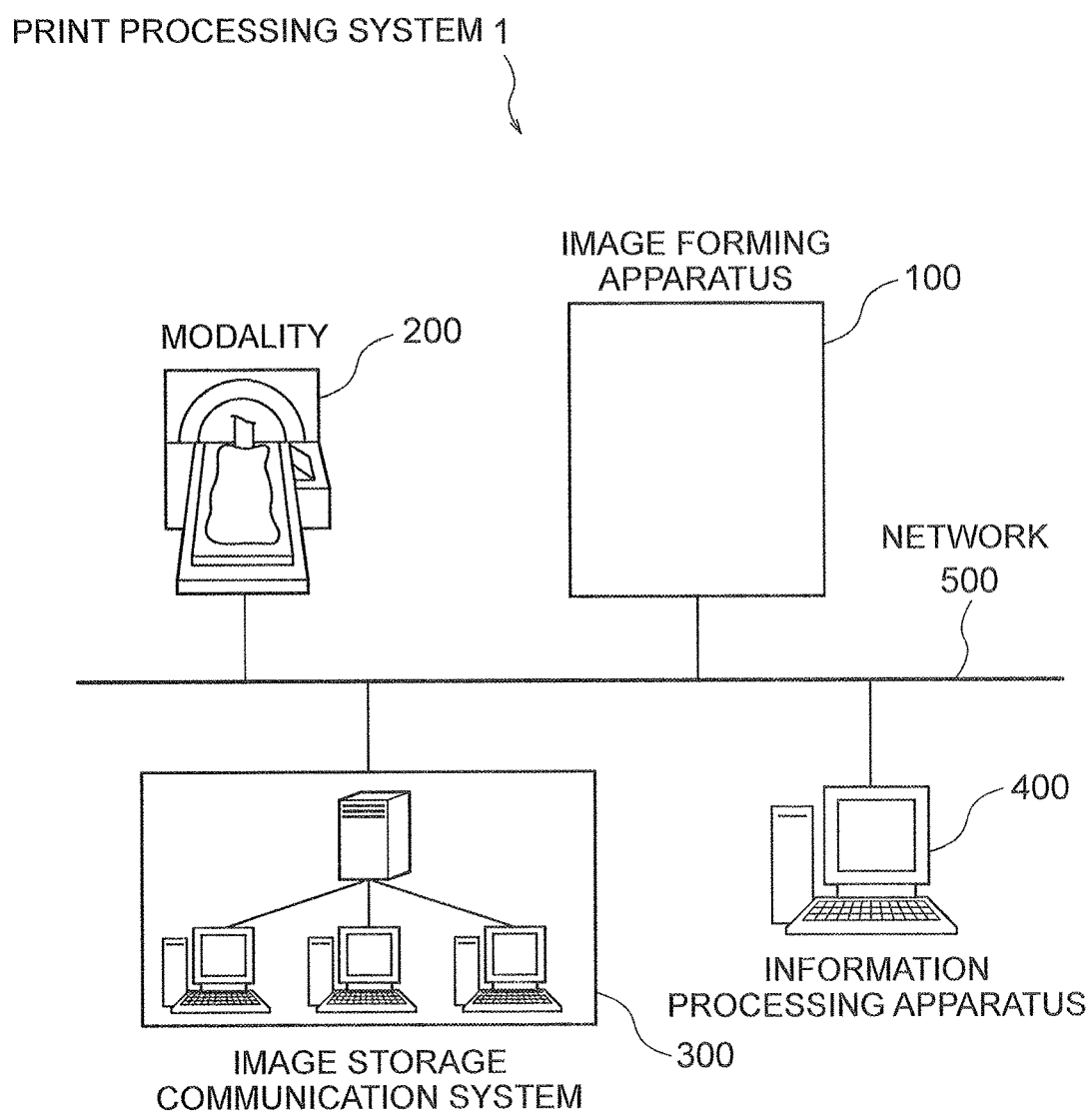
FIG. 2 is a block diagram showing a configuration of a print processing system including an image forming apparatus of the first embodiment.

FIG. 2 is a block diagram showing an entire configuration of a print processing system 1 including the image forming apparatus 100 as the image processing apparatus of the first embodiment. The print processing system 1 includes an image forming apparatus 100, a modality (i.e., a medical imaging apparatus) 200, an image storage communication system 300, and an information processing apparatus 400. The print processing system 1 further includes a network 500 connecting the image forming apparatus 100, the modality 200, the image storage communication system 300 and the information processing apparatus 400.

The modality 200 photographs an image, creates DICOM data including image data in accordance with the DICOM standard, and transmits the DICOM data to a specified apparatus (for example, the image forming apparatus 100) the network 500 in accordance with a protocol in accordance with the DICOM standard. The modality 200 may be, for example, an X-ray photographing apparatus, an ultrasonic photographing apparatus (Echography), a computerized topography (CT) or the like.

The image storage communication system 300 is also referred to as a PACS (Picture Archiving and Communication Systems). The image storage communication system 300 receives the DICOM data transmitted from the modality 200, stores the received DICOM data in a database, and manages the stored DICOM data. Further, the image storage communication system 300 reads out the DICOM data from the database in response to a request from another apparatus of the print processing system 1, displays the read DICOM data on a screen, and outputs the DICOM data to the image forming apparatus 100 if necessary.

The information processing apparatus 400 is, for example, a personal computer used for Office Automation (OA), i.e., used to print business documents. The network 500 is, for example, a LAN (Local Area Network).

Figure 3:
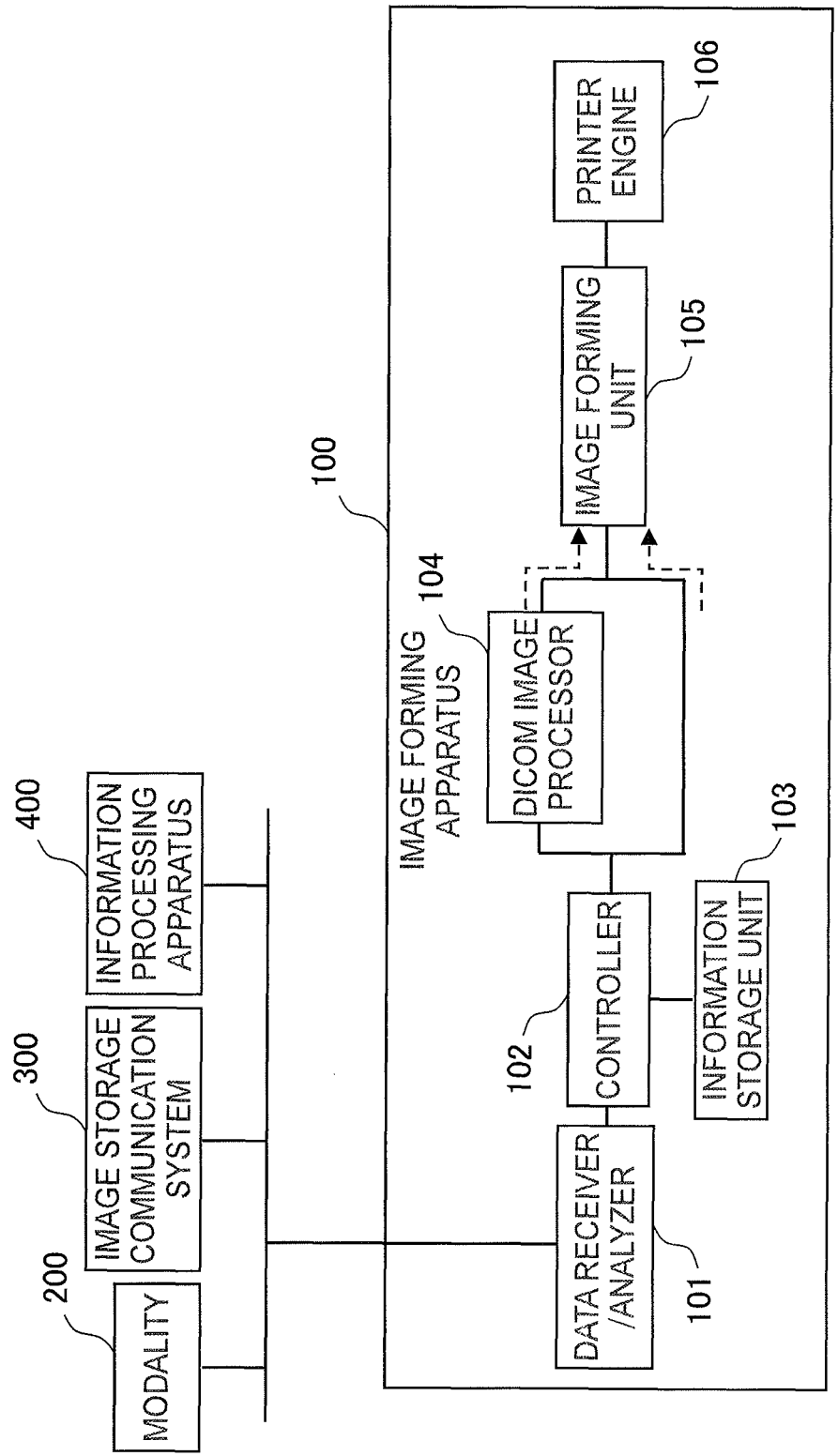
FIG. 3 is a block diagram showing a configuration of the image forming apparatus of the first embodiment.

FIG. 3 is a block diagram showing a configuration of the image forming apparatus 100 of the first embodiment. The image forming apparatus 100 is, for example, an electrophotographic printer. The image forming apparatus 100 includes a data receiver/analyzer 101 as a data receiver, a controller 102 as a setting unit and a determination unit, an information storage unit 103 as a setting storage unit, a DICOM image processor 104 as an image processor, an image forming unit 105 as a print controller, and a printer engine 106 as a print mechanism.

The data receiver/analyzer 101 receives the DICOM data from the modality 200 or the image storage communication system 300 through the network 500 using the protocol in accordance with the DICOM standard, and analyzes contents of the received data. In this regard, the data receiver/analyzer 101 may also receive print data (i.e., a business document or the like) other than the DICOM data from, for example, the information processing apparatus 400 through the network 500.

The controller 102 transmits the received data to a destination based on a result of analysis of the data receiver/analyzer 101. When the received data is DICOM data, the controller 102 transmits the received data to the DICOM image processor 104. When the received data is not DICOM data, the controller 102 transmits the received data to the image forming unit 105.

Figure 4:
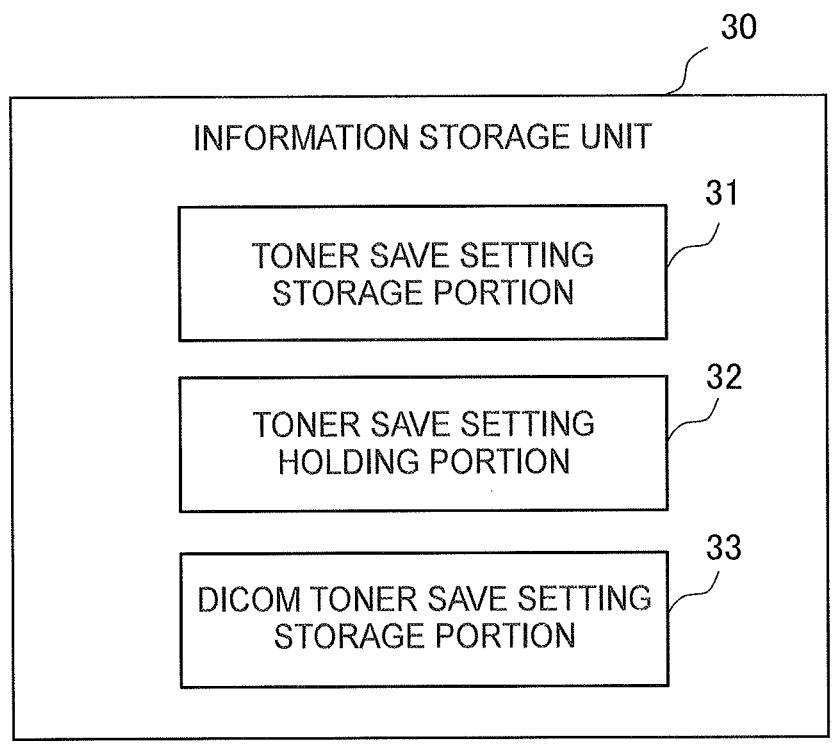
FIG. 4 is a schematic view showing a configuration of an information storage unit of the image forming apparatus of the first embodiment.

The information storage unit 103 stores information on settings of the toner save function. FIG. 4 shows a configuration of the information storage unit 103. The information storage unit 103 includes a toner save setting storage portion 31 as a setting storage unit, a toner save setting holding portion 32, and a DICOM toner save setting storage portion 33.

The toner save setting storage portion 31 stores information on whether the toner save function of the image forming apparatus 100 is enabled or disabled by an apparatus administrator (or a user). In the toner save setting storage portion 31, whether the toner save function is enabled (i.e., ON) or disabled (i.e., OFF) is represented by, for example, a flag. When the toner save function is enabled, an entire image is printed in a toner save mode except in the case where a medical image is to be printed as described later. When the toner save function is disabled, an entire image is printed in a normal mode.

Here, the toner save mode (i.e., a first print mode) is a print mode in which toner is saved, i.e., an amount of toner consumption is reduced. The normal mode (i.e., a second print mode) is a print mode in which the amount of toner consumption is larger than in the toner save mode and a high quality image is printed. Hereinafter, the setting of whether the toner save function is enable or disabled will be referred to as a toner save setting of the apparatus.

The toner save setting holding portion 32 temporarily holds the toner save setting stored in the toner save setting storage portion 31. Since the toner save setting storage portion 31 may be reset as described later, the toner save setting holding portion 32 is configured to store the setting stored in the toner save setting storage portion 31 before the reset.

The DICOM toner save setting storage portion 33 stores a DICOM toner save setting. In the DICOM toner save setting storage portion 33, whether the DICOM toner save setting is ON or OFF is represented by, for example, a flag.

When the DICOM toner save is enabled (ON), a region of the medical image to be used by the doctor in image diagnosis (i.e., the diagnostic image region 11) is printed with high quality in the normal mode, and the margin region 12 (i.e., a region where no image is printed) is provided outside the diagnostic image region 11 as shown in FIG. 10. When the DICOM toner save is disabled (OFF), the medical image is entirely printed in the normal mode.

Figure 5:
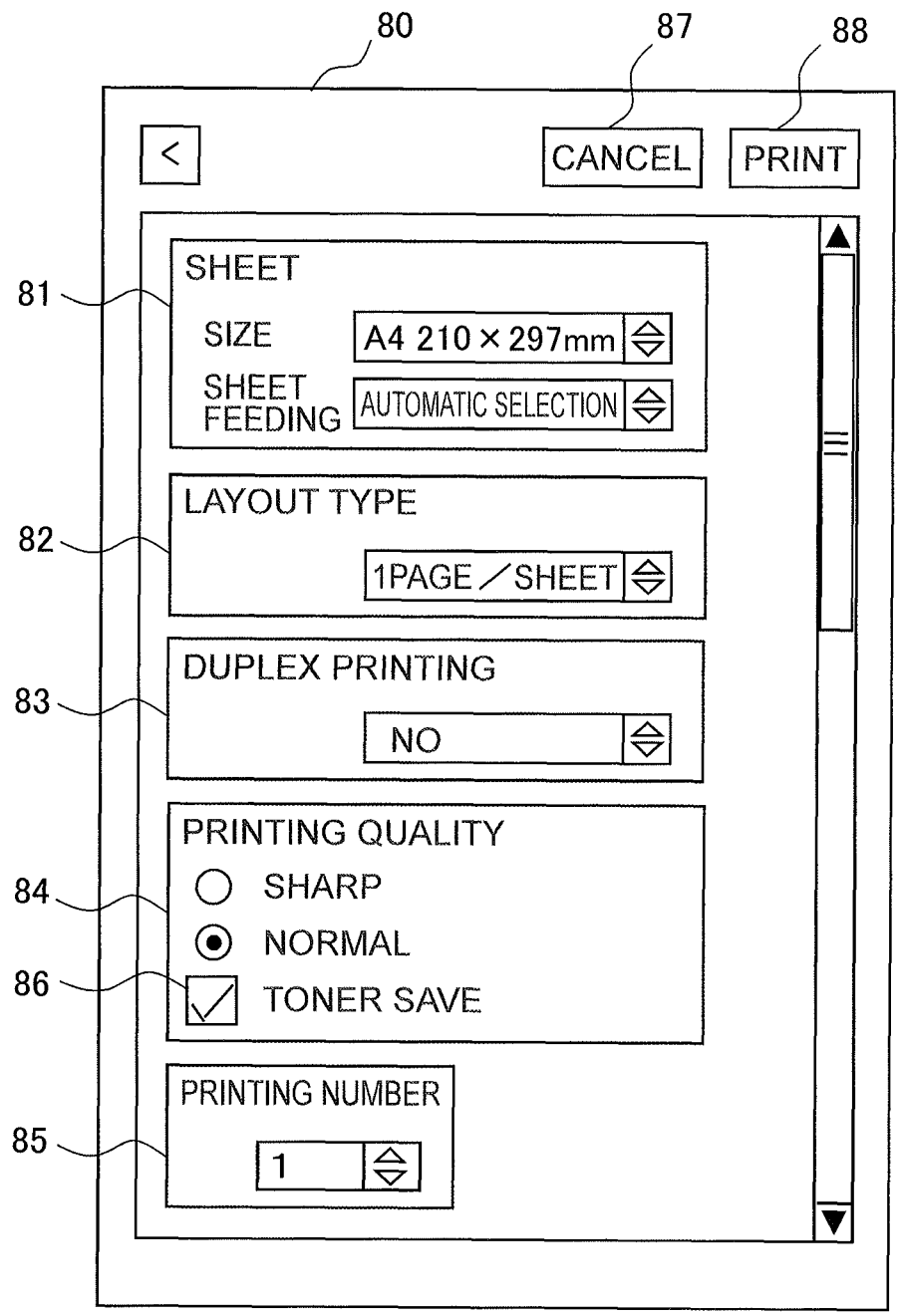
FIG. 5 is a schematic view showing an example of a setting screen of a toner save function of the first embodiment.

FIG. 5 is a schematic view showing an example of the setting screen 80 for setting the toner save function of the image forming apparatus 100. The setting to enable or disable the toner save function of the image forming apparatus 100 can be performed using the setting screen 80. The setting screen 80 is displayed on a display screen of the modality 200, the image storage communication system 300 or the information processing apparatus 400 through the network 500 under control of the controller 102. The setting screen 80 may be displayed on a display screen of the image forming apparatus 100 under control of the controller 102.

The setting screen 80 shown in FIG. 5 includes a medium size setting unit 81, a layout type setting unit 82, a duplex printing setting unit 83, a printing quality setting unit 84, and a printing number setting unit 85. A toner save setting unit 86 is provided in the printing quality setting unit 84. The toner save setting unit 86 includes, for example, a checkbox for setting whether or not to enable the toner save function of the image forming apparatus 100. In this regard, the setting screen 80 is required to accept setting to enable/disable the toner save function of the image forming apparatus 100, and is not limited to a configuration shown in FIG. 5.

Figure 6:
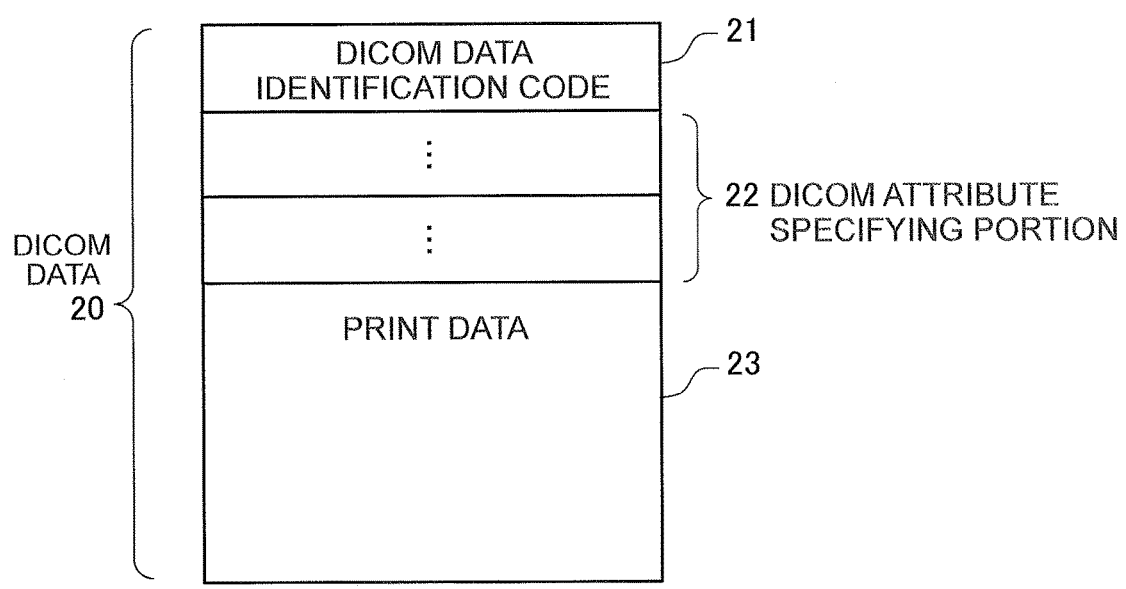
FIG. 6 is a schematic view showing contents of DICOM data of the first embodiment.

FIG. 6 is a schematic view showing contents of the DICOM data 20 received by the data receiver/analyzer 101 through the network 500. The DICOM data 20 includes a DICOM data identification code 21, a DICOM attribute specifying portion 22, and print data 23 which are arranged in this order from a head of the DICOM data 20.

The DICOM data identification code 21 (i.e., attribute information) is an identification code indicating that the data is DICOM data. The data receiver/analyzer 101 of the image forming apparatus 100 determines whether the received data is DICOM data or not by referring to the DICOM data identification code 21 of the received data.

The print data 23 includes a medical image (i.e., a DICOM image) as image data. The DICOM attribute specifying portion 22 includes information indicating a range of the diagnostic image region 11 of the medical image included in the print data 23 to be used by the doctor in image diagnosis. The DICOM attribute specifying portion 22 also includes associated information such as patient information, a photographing day or the like. Description of the associated information is omitted.

Returning back to FIG. 3, the DICOM image processor 104 is configured to create image data from the medical image included in the received DICOM data. When the received data is DICOM data and when the toner save function of the image forming apparatus 100 is enabled (ON), the DICOM image processor 104 processes image data so as to change the region around the diagnostic image region 11 (i.e., the region to be used by the doctor in image diagnosis) into the margin region 12.

The image forming unit 105 is a print controller that receives image data transmitted from the DICOM image processor 104 or the controller 102, transmits the image data to the printer engine 106, and causes the printer engine 106 to print the image data. When the toner save function of the image forming apparatus 100 is enabled (ON), the image forming unit 105 creates image data for the toner save mode by thinning out dots in order to reduce the amount of toner consumption.

The printer engine 106 prints the image data transmitted from the image forming unit 105 on a medium such as a print sheet. In a particular example, the printer engine 106 forms a toner image (i.e., a developer image) on the medium using electrophotography.

To be more specific, the printer engine 106 includes an image bearing body such as a photosensitive drum, a charging unit that uniformly charges a surface of the image bearing body, an exposure unit that emits light to expose the surface of the image bearing body to form an electrostatic latent image, a developing unit that develops the latent image with toner (developer), a transfer unit that transfers a toner image (i.e., a developer image) from the surface of the image bearing body to the medium, and a fixing unit that fixes the toner image to the medium. Use of LEDs (Light Emitting Diodes) in the exposure unit has an advantage in obtaining a high definition image.

Among components of the image forming apparatus 100, the data receiver/analyzer 101, the controller 102, the information storage unit 103, the DICOM image processor 104 and the image forming unit 105 constitute an image forming controller. The DICOM image processor 104 and the image forming unit 105 constitute an image processing unit (or an image processor) that performs processing to print an image.

<Operation>

Next, an operation of the image forming apparatus 100 of the first embodiment will be described. Here, operations of the controller 102, the DICOM image processor 104 and the image forming unit 105 will be described with reference to flowcharts.

Figure 7:
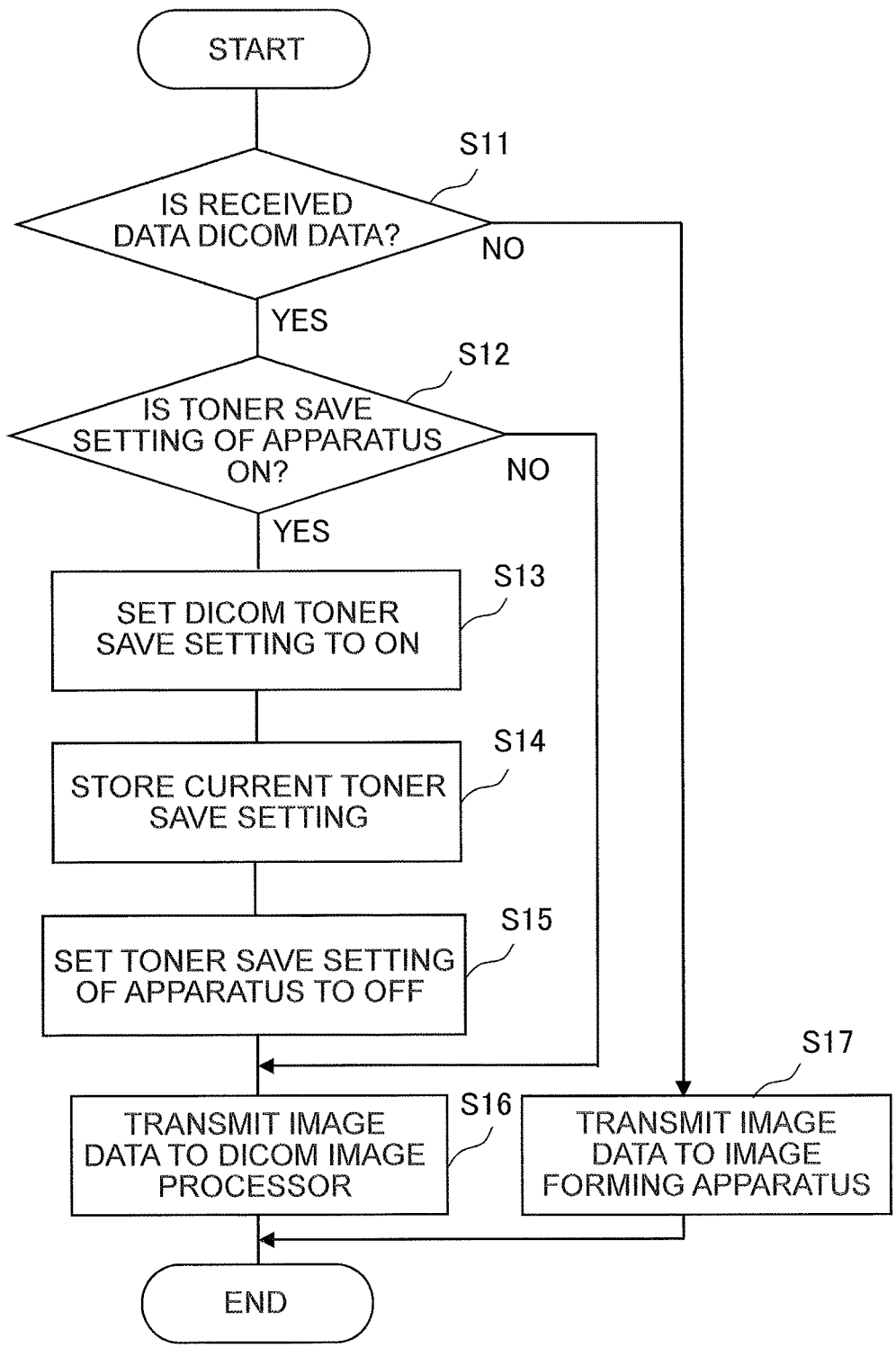
FIG. 7 is a flowchart showing processing of a controller of the image forming apparatus of the first embodiment.

FIG. 7 is a flowchart showing processing of the controller 102. When the data receiver/analyzer 101 receives data through the network 500, the data receiver/analyzer 101 determines whether the received data includes the DICOM data identification code 21, and outputs a determination result. The controller 102 determines whether the received data is DICOM data or not based on the determination result of the data receiver/analyzer 101 (i.e., step S11).

When the received data is DICOM data (YES in step S11), the controller 102 proceeds to step S12. When the received data is not DICOM data (NO in step S11), the controller 102 proceeds to step S17.

In step S12, the controller 102 checks the toner save setting stored in the toner save setting storage portion 31 of the image forming apparatus 100. When the toner save setting stored in the toner save setting storage portion 31 is ON (YES in step S12), the controller 102 proceeds to step S13. When the toner save setting is OFF (NO in step S12), the controller 102 proceeds to step S16.

In step S13, the controller 102 stores ON (enabled) as the DICOM toner save setting in the DICOM toner save setting storage portion 33. Then, the controller 102 copies a current toner save setting of the toner save setting storage portion 31, and stores the copied toner save setting in the toner save setting holding portion 32 (step S14).

Then, the controller 102 changes the toner save setting stored in the toner save setting storage portion 31 to OFF (step S15). Then, the controller 102 transmits image data extracted from the data received by data receiver/analyzer 101 to the DICOM image processor 104 (step S16), and terminates the processing.

In contrast, in the above-described step S11, when the received data is not DICOM data, the controller 102 transmits the image data received by the data receiver/analyzer 101 to the image forming unit 105 (step S17), and terminates the processing.

In this way, in the processing shown in FIG. 7, when the received data is DICOM data and when the toner save setting of the apparatus (i.e., the toner save setting stored in the toner save setting storage portion 31) is ON, the toner save setting of the apparatus is set to OFF, so that printing is not performed in the toner save mode.

Figure 8:
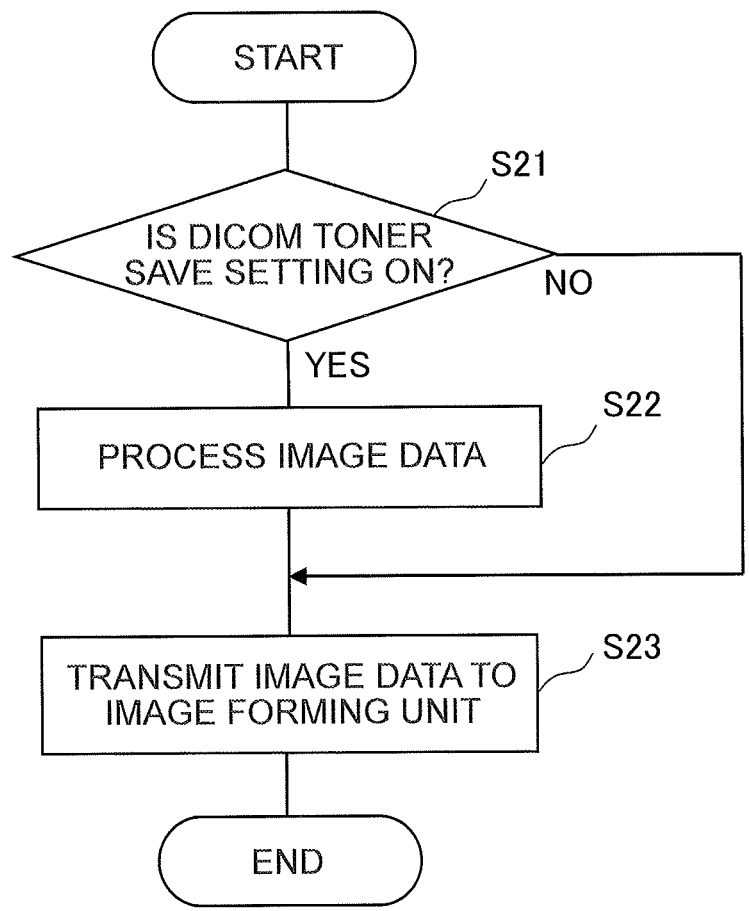
FIG. 8 is a flowchart showing processing of a DICOM image processor of the image forming apparatus of the first embodiment.

FIG. 8 is a flowchart showing processing of the DICOM image processor 104. The DICOM image processor 104 refers to the DICOM toner save setting storage portion 33, and determines whether the DICOM toner save setting is ON (enabled) or not (step S21). When the DICOM toner save setting is ON, the DICOM image processor 104 proceeds to step S22. When the DICOM toner save setting is OFF (disabled), the DICOM image processor 104 proceeds to step S23.

In step S22, the DICOM image processor 104 processes the image data transmitted from the controller 102 so as to change the region around the diagnostic image region 11 to the margin region 12 (step S22). For example, in the case of an X-ray photograph, a region of a black background surrounding the diagnostic image region 11 from four sides is changed to the margin region 12.

For example, when printing is performed on the print sheet of A4 size, the diagnostic image region 11 is formed at a center portion of the print sheet in a printing direction (i.e., a vertical direction) and in a widthwise direction (i.e., a horizontal direction). The margin region 12 is formed on each of upper, lower, right and left sides of the diagnostic image region 11. A range of the diagnostic image region 11 in the medial image is specified by the DICOM attribute specifying portion 22 included in the DICOM data 20.

Then, the DICOM image processor 104 transmits image data to the image forming unit 105 (step S23), and terminates the processing.

Figure 9:
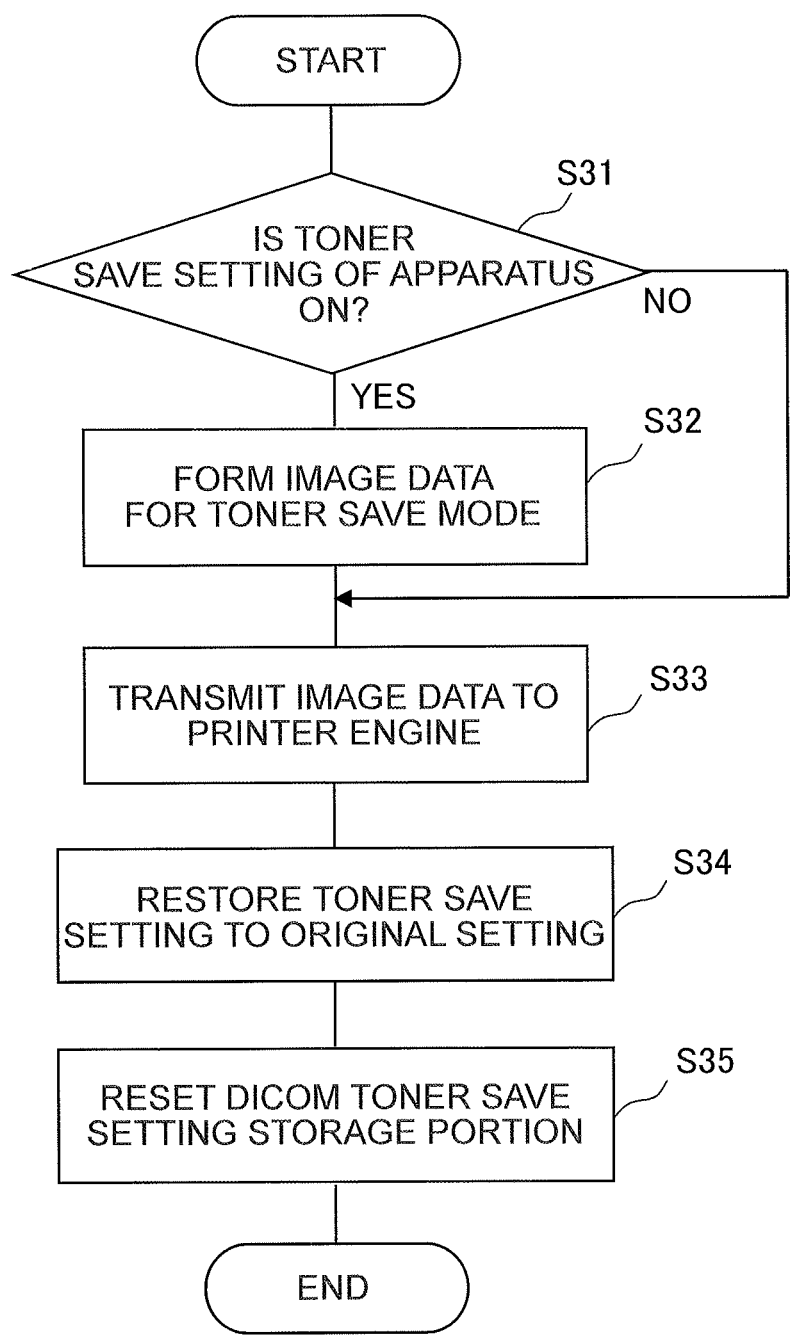
FIG. 9 is a flowchart showing processing of an image forming unit of the image forming apparatus of the first embodiment.

FIG. 9 is a flowchart showing processing of the image forming unit 105. First, the image forming unit 105 checks whether the toner save setting of the apparatus stored in the toner save setting storage portion 31 is ON (enabled) or not (step S31). When the toner save setting is ON (YES in step 31), the image forming unit 105 proceeds to step S32. When the toner save setting is OFF (NO in step 31), the image forming unit 105 proceeds to step S33.

In step S32, the image forming unit 105 creates image data for the toner save mode so that an entire image becomes lighter (i.e., a density of the entire image decreases). The image data for the toner save mode can be created by, for example, thinning out dots forming an image. In this regard, in the case of DICOM data, the step S32 is not performed since the toner save setting of the apparatus (i.e., the toner save setting stored in the toner save setting storage portion 31) is set to OFF in step S15 shown in FIG. 7 as described above.

Then, the image forming unit 105 transmits the created image data to the printer engine 106 (step S33). The printer engine 106 prints the image data transmitted from the image forming unit 105 on the print sheet using the toner.

To be more specific, when the DICOM toner save setting is ON, the diagnostic image region 11 of the medical image 10 (shown in FIG. 10) is printed with high quality in the normal mode, and the margin region 12 is formed around the diagnostic image region 11. When the DICOM toner save setting is OFF, the medical image 10 is entirely printed with high quality in the normal mode. When the received data is not DICOM data, and when the toner save setting of the apparatus is ON, an image is entirely printed in the toner save mode. When the received data is not DICOM data, and when the toner save setting of the apparatus is OFF, an image is entirely printed in the normal mode.

After printing of all the received data is completed, the image forming unit 105 stores the toner save setting (stored in the toner save setting holding portion 32) in the toner save setting storage portion 31 (step S34), and resets the DICOM toner save setting in the DICOM toner save setting storage portion 33 to OFF (disabled) (step S35).

In this way, the toner save setting stored in the toner save setting storage portion 31 is returned to an original setting (i.e., the toner save setting held in the toner save setting holding portion 32). Therefore, when the data (for example, a general business document) which is not DICOM data is to be printed afterward, the printing is performed in accordance with the toner save setting of the apparatus which has been set by the apparatus administrator.

<Advantages of Embodiment>

According to the first embodiment of the present invention, when the received data is DICOM data, and when the toner save function of the image forming apparatus 100 is set to ON (enabled) by the apparatus administrator, printing is performed while providing the margin region 12 outside the diagnostic image region 11 of the medical image 10. Since the margin region 12 is provided, an amount of toner consumption can be reduced. Further, since the diagnostic image region 11 is printed in the normal mode (i.e., not in the toner save mode), the diagnostic image region 11 can have high image quality. For example, the black color can be deeply printed.

In this way, the amount of toner consumption can be reduced without reducing the image quality of the diagnostic image region 11. Therefore, a demand of the doctor and a demand of the apparatus administrator are both satisfied.

Further, the diagnostic image region 11 included in the medical image is specified by information included in the DICOM attribute specifying portion 22 of the DICOM data 20. Therefore, a region necessary for image diagnosis can be correctly specified, and a region unnecessary for image diagnosis can be changed to the margin region 12.

Moreover, when the diagnostic image region 11 is printed in the normal mode while providing the margin region 12 as described above, the toner save setting stored in the toner save setting storage portion 31 is once set to OFF (disabled), but is returned to the original setting after the printing is completed. Therefore, when the data which is not DICOM data is to be printed afterward, the printing can be performed according to the setting which has been set by the apparatus administrator, with the result that the amount of toner consumption can be reduced.

In the above description, a determination whether the received data is DICOM data or not is performed based on the DICOM data identification code 21 shown in FIG. 6 (step S11 in FIG. 7). However, the first embodiment is not limited to such an example. For example, it is also possible to determine whether the received data is DICOM data or not based on a reception port number.

The reception port number is a sub-address at a lower level than an IP address, and is provided for connecting with a plurality of communication partners at the same time in internet communication. For example, "Port 9100" or the like is generally used as a reception port number for data. "Port 10001" or the like is used as a reception port number for DICOM data. The controller 102 may determine whether the received data is DICOM data or not based on the reception port number.

MODIFICATIONS

Various modifications or changes may be made to the above described first embodiment.

FIG. 10 is a block diagram showing a first modification of the first embodiment. In the first embodiment, the image forming apparatus 100 includes the data receiver/analyzer 101, the controller 102, the information storage unit 103, the DICOM image processor 104 and the image forming unit 105. In contrast, in the first modification shown in FIG. 10, a host device 100A of an image forming apparatus 600 includes the data receiver/analyzer 101, the controller 102, the information storage unit 103, the DICOM image processor 104 and the image forming unit 105.

In the first modification of FIG. 10, the host device 100A transmits print command and image data to the image forming apparatus 600, and the image forming apparatus 600 prints the image data according to the print command. When the host device 100A receives DICOM data, and when the toner save setting of the apparatus is ON (enabled), the host device 100A causes the image forming apparatus 600 to perform printing while providing the margin region 12 outside the diagnostic image region 11. Therefore, the amount of toner consumption can be reduced without reducing the image quality of the diagnostic image region 11.

In FIG. 10, the host device 100A and the image forming apparatus 600 are directly connected with each other. However, the host device 100A may be configured to transmit the print command and the image data to the image forming apparatus 600 through the network 500.

Figure 11A:
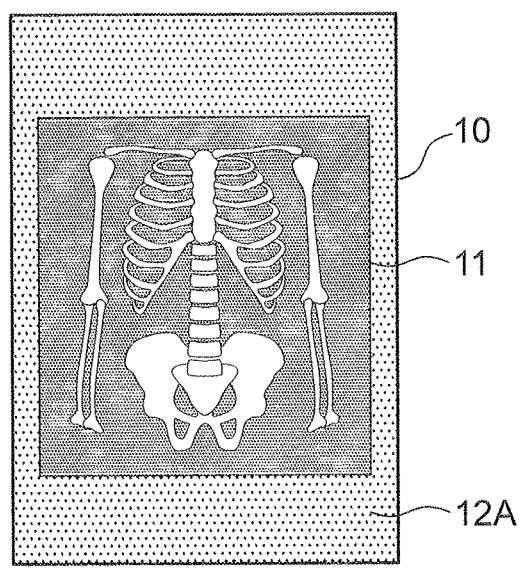
FIGS. 11A and 11B are schematic views for illustrating second and third modifications of the first embodiment.

FIG. 11A is a schematic view showing a second modification of the first embodiment. In the first embodiment, no toner is printed in the margin region 12 (FIG. 10) outside the diagnostic image region 11. However, for example, a toner save region 12A (i.e., a low density region) where dots are thinned out may be provided outside the diagnostic image region 11 as shown in FIG. 11A. Further, it is also possible that a way of thinning out the dots is selectable.

Figure 11B:
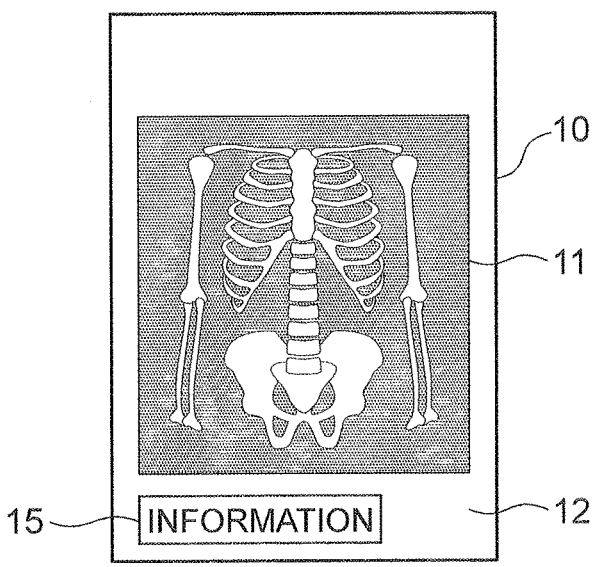

FIG. 11B is a schematic view showing a third modification of the first embodiment. The DICOM attribute specifying portion (FIG. 6) of the DICOM data includes associated information such as patient information, a photographing day or the like. The associated information 15 may be printed in the margin region 12 as shown in FIG. 11B. In this case, the associated information 15 may be printed with high quality in the normal mode (i.e., not in the toner save mode).

Figure 12:
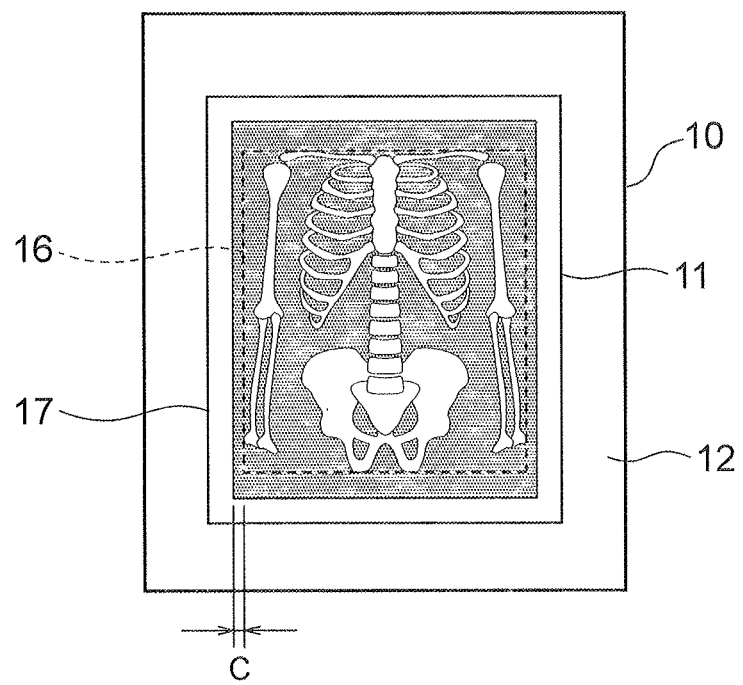
FIG. 12 is a schematic view for illustrating a fourth modification of the first embodiment.

FIG. 12 is a schematic view showing a fourth modification of the first embodiment. In the first embodiment, the margin region 12 (FIG. 1C) is provided outside the region specified by the DICOM attribute specifying portion 22 (FIG. 6). However, as shown in FIG. 12, within a region 17 specified by the DICOM attribute specifying portion 22 (FIG. 6), a frame 16 of an effective screen may be detected using, for example, image processing. A region outside the frame 16 and distanced from the frame 16 by a certain distance C (for example, 1 cm) or more may be changed to the margin region 12 or changed to the toner save region 12A (see FIG. 11A). Further, a frame line indicating the region 17 may also be printed. The distance C may be changeable. In FIGS. 11A, 11B and 12, the black background of the diagnostic image region 11 is indicated by dots.

Figure 13:
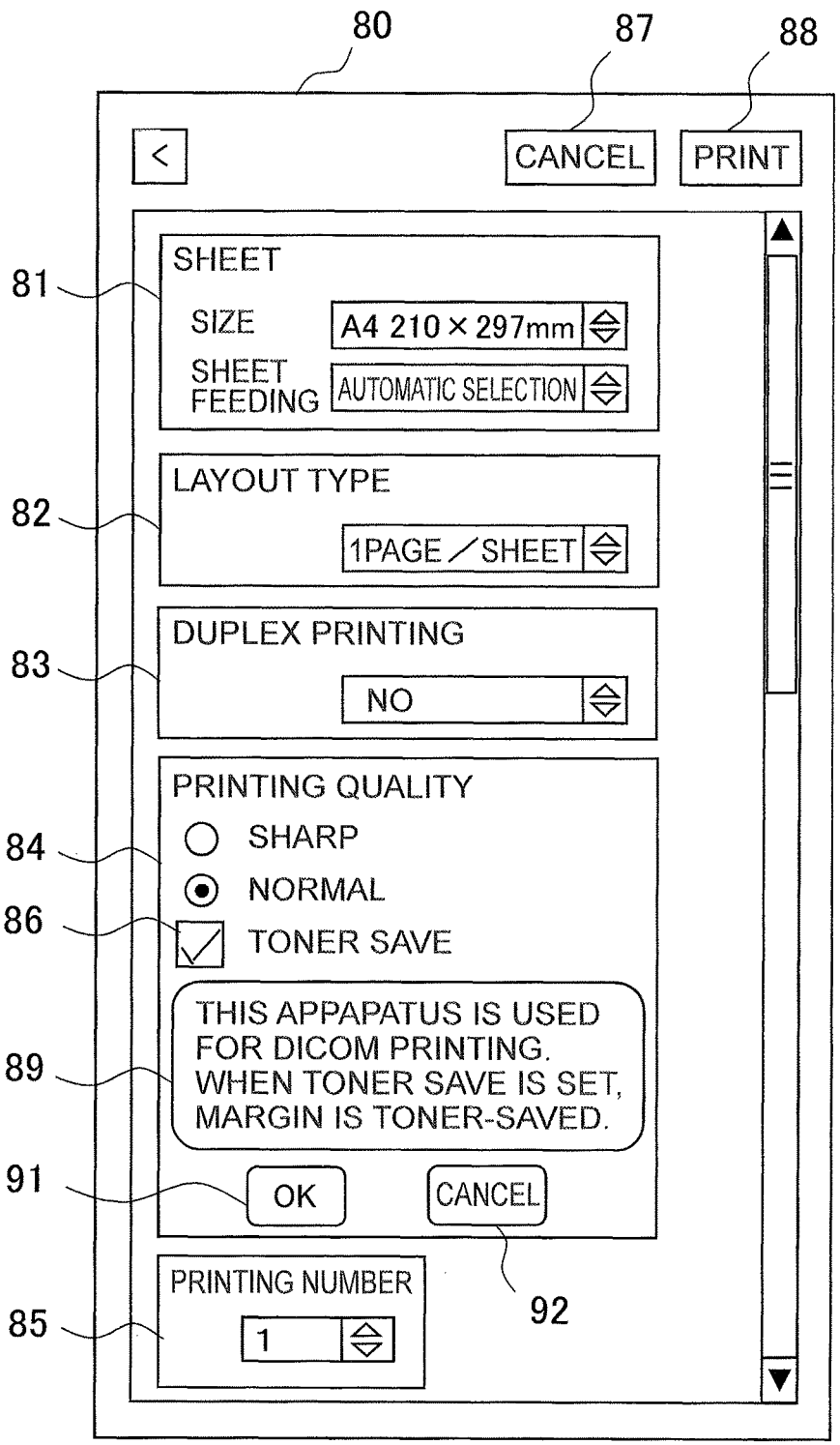
FIG. 13 is a schematic view showing a setting screen of a toner save function of a fifth modification of the first embodiment.

FIG. 13 is a schematic view showing a fifth modification of the first embodiment. As shown in FIG. 13, when the toner save function is to be enabled using the setting screen 80 (see FIG. 5), a message 89 may be displayed on the setting screen 80 as shown in FIG. 13. The message 89 may read, for example, "This apparatus is used for DICOM printing. When toner save is set, a margin region is toner-saved."

For example, the information storage unit 103 (FIG. 4) may be added with a storage unit (i.e., a print storage unit, or a history storage unit) that stores information on whether the image forming apparatus 100 has ever printed a medical image (i.e., a DICOM image) using a flag or the like. The message 89 may be displayed when the checkbox of the toner save setting unit 86 (FIG. 13) is checked and in the case where the image forming apparatus 100 has ever printed the medical image.

Further, as shown in FIG. 13, an OK button 91 and a cancel button 92 may be displayed on the setting screen 80 as well as the message 89. The OK button 91 is used to determine the setting of the toner save function. The cancel button 92 is used to cancel the setting of the toner save function. With such an arrangement, the apparatus administrator or the like who sees the message 89 can determine or cancel the setting of the toner save function.

Figure 14:
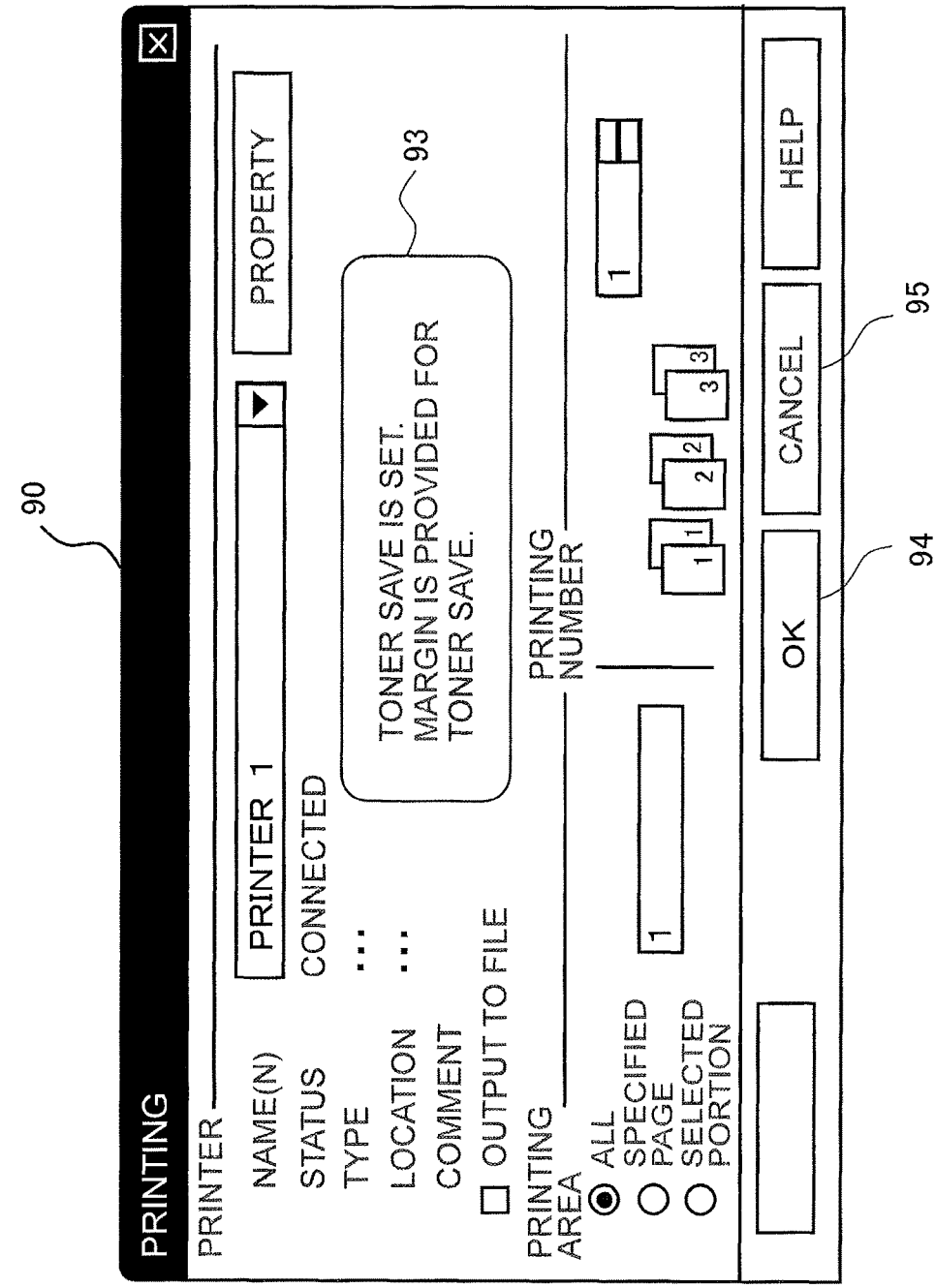
FIG. 14 is a schematic view showing a print instruction screen of a sixth modification of the first embodiment.

FIG. 14 is a schematic view showing a sixth modification of the first embodiment. When the medical image is to be printed from the modality 200 or the like in the state where the toner save function of the image forming apparatus 100 is set, a message 93 may be displayed on, for example, a print instruction screen 90 as shown in FIG. 14. The message 93 may read "Toner save is set. Margin region is provided for toner save." Furthermore, an OK button 94 and a cancel button 95 may be displayed on the print instruction screen 90 as well as the message 93. The OK button 94 is used to determine the setting of the toner save function. The cancel button 95 is used to cancel the setting of the toner save function.

The print instruction screen 90 (FIG. 14) may be displayed on, for example, a monitor screen of the apparatuses (i.e., the modality 200, the image storage communication system 300 and the information processing apparatus 400) connected to the network 500 by means of a web server unit (not shown) under control of the controller 102.

The image forming apparatus 100 may be a color image formation apparatus (for example, a color printer) configured to form an image using the toner of yellow (Y), magenta (M), cyan (C) and black (K). Generally, a black color can be obtained by combining yellow toner, magenta toner and cyan toner, even if the image forming apparatus 100 runs out of black toner. However, in the case of printing the DICOM image, a quality of black color is important. Therefore, the image forming apparatus 100 may be configured to stop printing when the image forming apparatus 100 runs out of black toner, and displays a message indicating running out of the black toner. With such an arrangement, a quality of the black color can be enhanced.

The image processing apparatus of the present invention is applicable to, for example, an image forming apparatus such as a printer, MFT (Multifunction Peripheral) or the like, or a host device that transmits image data to the image forming apparatus.

While the preferred embodiments of the present invention have been illustrated in detail, it should be apparent that modifications and improvements may be made to the invention without departing from the spirit and scope of the invention as described in the following claims.

What is claimed is:

1. An image processing apparatus comprising:
   a setting unit that accepts ON or OFF of a toner save setting of the image processing apparatus;
   a data receiver configured to receive DICOM data in accordance with DICOM standard using a protocol in accordance with the DICOM standard;
   a determination unit that determines whether received data is DICOM data or normal data; and
   an image processing unit configured to perform processing to print an image in a toner save mode for saving developer or to print an image in a normal mode that uses a larger amount of developer than the toner save mode, according to a toner save setting of the image processing apparatus,
   wherein when the toner save setting of the image processing apparatus is OFF, the image processing unit performs processing to print an image in the normal mode in either case whether the received data is DICOM data or normal data, wherein when the toner save setting of the image processing apparatus is ON and the received data is normal data, the image processing unit performs processing to print an entire image included in the normal data in the toner save mode, and wherein when the toner save setting of the image processing apparatus is ON and the received data is DICOM data, the image processing unit performs processing to print a diagnostic image region of a medical image included in the DICOM data in the normal mode.

2. The image processing apparatus according to claim 1, wherein when the toner save setting of the image processing apparatus is ON and the received data is DICOM data, the image processing unit changes a region outside the diagnostic image region to a margin region.

3. The image processing apparatus according to claim 1, wherein when the toner save setting of the image processing apparatus is ON and the received data is DICOM data, the image processing unit performs processing to print a region outside the diagnostic image region in the toner save mode.

4. The image processing apparatus according to claim 1, wherein the diagnostic image region of the medical image is specified based on attribute information included in the DICOM data.

5. The image processing apparatus according to claim 4, wherein the image processing unit performs processing to print a region within the diagnostic image region specified by the attribute information and outside a frame surrounding an effective image in a mode in which developer is saved.

6. The image processing apparatus according to claim 1, further comprising a setting storage unit that stores the toner save setting of the image processing apparatus,
wherein the toner save setting of the image processing apparatus stored in the setting storage unit is changed from ON to OFF when the medical image is printed.

7. The image processing apparatus according to claim 6, wherein the toner save setting of the image processing apparatus stored in the setting storage unit is returned to ON after the medical image is printed.

8. The image processing apparatus according to claim 1, wherein when the image processing unit performs processing to print the medical image, the image processing unit performs processing to print associated information included in the DICOM data outside the diagnostic image region.

9. The image processing apparatus according to claim 1, wherein the setting unit displays a setting screen for the toner save setting of the image process apparatus,
wherein when the toner save setting of the image processing apparatus is set to ON in the setting screen, the setting screen further displays a message indicating that developer is saved outside the diagnostic image region of the medical image.

10. The image processing apparatus according to claim 9, further comprising a print storage unit that stores information on whether the image processing apparatus has ever printed the medical image included in the DICOM data,
wherein when the toner save setting of the image processing apparatus is ON, a message is displayed according to information stored in the print storage unit, the message indicating that the image processing apparatus is also used to print the medical image.

11. The image processing apparatus according to claim 10, wherein in the case where the print storage unit stores information indicating that the image processing apparatus has printed the medical image included in the DICOM data, the setting screen displays the message, and
wherein in the case where the print storage unit does not store information indicating that the image processing apparatus has ever printed the medical image included in the DICOM data, the setting screen does not display the message.

12. The image processing apparatus according to claim 1, wherein the image processing apparatus is configured as an image forming apparatus.

13. The image processing apparatus according to claim 1, wherein the image processing apparatus is configured as a host device that instructs an image forming apparatus to perform printing.

14. The image processing apparatus according to claim 1, wherein when the toner save setting of the image processing apparatus is ON and the received data is DICOM data, the image processing unit performs processing to print a region outside the diagnostic image region in the toner save mode, and to print associated information of the DICOM data in the region in the normal mode.

15. The image processing apparatus according to claim 1, wherein when the image processing unit runs out of black developer and the received data is normal data, the image processing unit performs processing to print a black image included in the normal data by mixing a plurality of colors, and
wherein when the image processing unit runs out of black developer and the received data is DICOM data, the image processing unit does not perform processing to print.

* * * * *